United States Patent [19]

Abrams

[11] Patent Number: 5,492,119
[45] Date of Patent: Feb. 20, 1996

[54] CATHETER TIP STABILIZING APPARATUS

[75] Inventor: Robert M. Abrams, Carlsbad, Calif.

[73] Assignee: Heart Rhythm Technologies, Inc., Temecula, Calif.

[21] Appl. No.: 172,039

[22] Filed: Dec. 22, 1993

[51] Int. Cl.⁶ .................................................. A61B 5/04
[52] U.S. Cl. .......................................... 128/642; 607/128
[58] Field of Search ............................ 128/642; 607/122, 607/123, 125–128, 132

[56] References Cited

U.S. PATENT DOCUMENTS

| | | | |
|---|---|---|---|
| 3,087,486 | 4/1963 | Kilpatrick | 128/642 |
| 4,103,690 | 8/1978 | Harris | 607/128 |
| 4,294,258 | 10/1981 | Bernard | 128/642 X |
| 4,565,200 | 1/1986 | Cosman | 128/642 |
| 5,237,996 | 8/1993 | Waldman et al. | 128/642 |
| 5,327,889 | 7/1994 | Imran | 607/122 X |

FOREIGN PATENT DOCUMENTS 1316072  5/1973  United Kingdom .................... 128/642

OTHER PUBLICATIONS

Elecath Cardiovascular Cathers and Instruments Catalog 1972, pp. 1–21.

Primary Examiner—George Manuel
Assistant Examiner—Jeffrey R. Jastrzab
Attorney, Agent, or Firm—Fulwider Patton Lee & Utecht

[57] ABSTRACT

Electrophysiology catheter apparatus including at least one retractable control wire with a preformed curved resilient foot formed at the distal extremity, slidably advanced and retracted within a longitudinal lumen of a catheter tube for controllably anchoring to a selected endocardial heart tissue. The proximal end of the control wire is formed with a handle to be grasped to slidably advance the preformed resilient foot beyond the distal tip of a catheter to project laterally to contact the adjacent tissue.

10 Claims, 2 Drawing Sheets

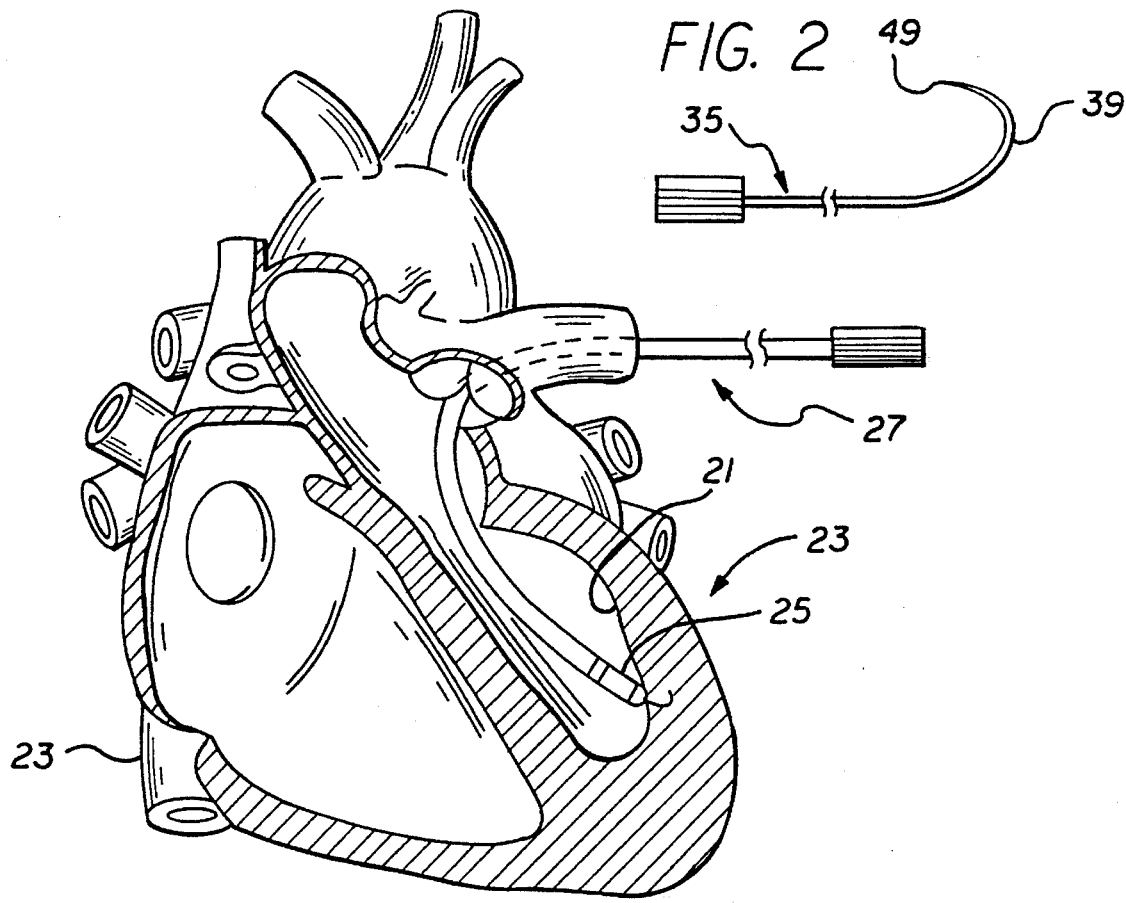
FIG. 2
FIG. 1
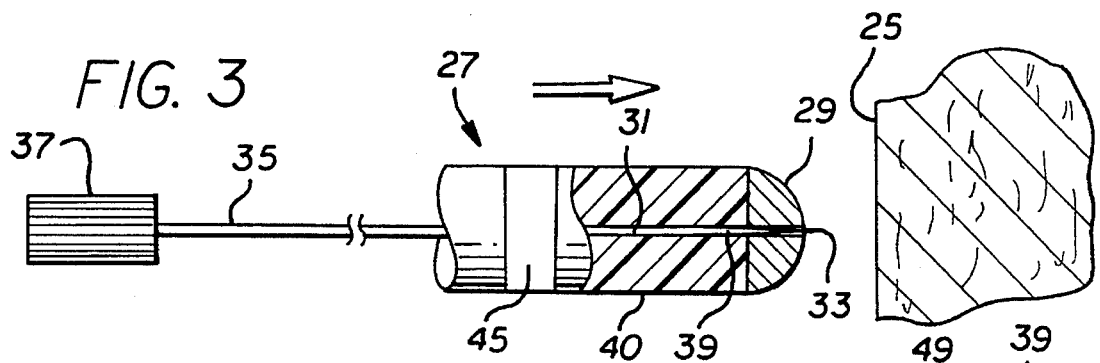
FIG. 3
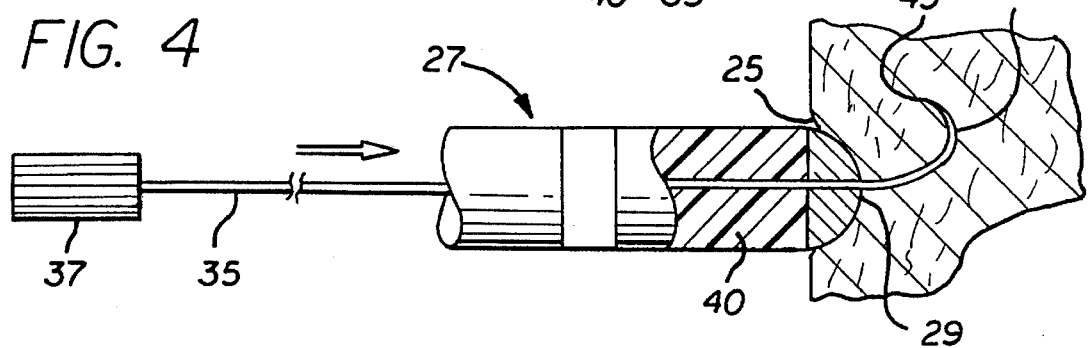
FIG. 4

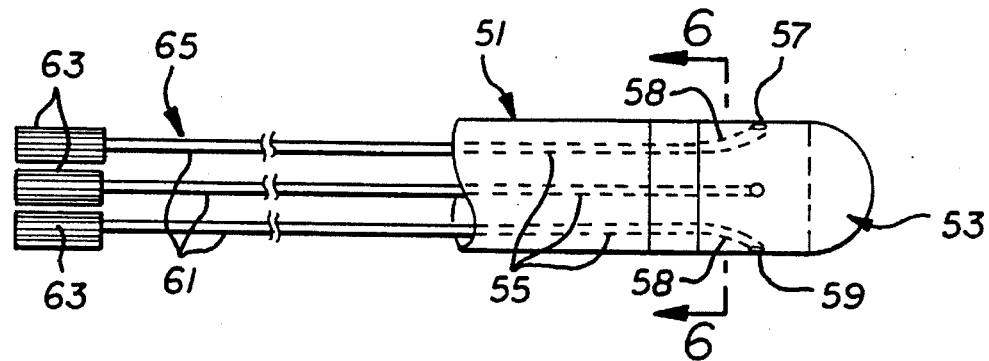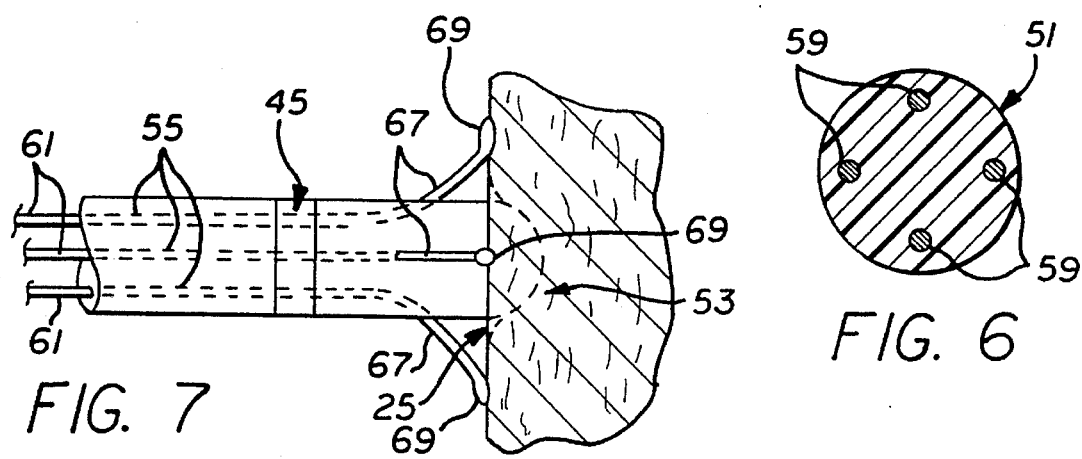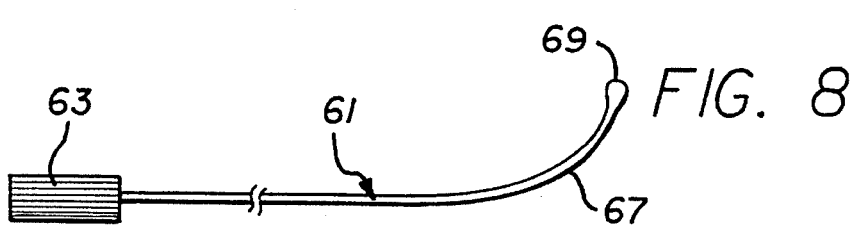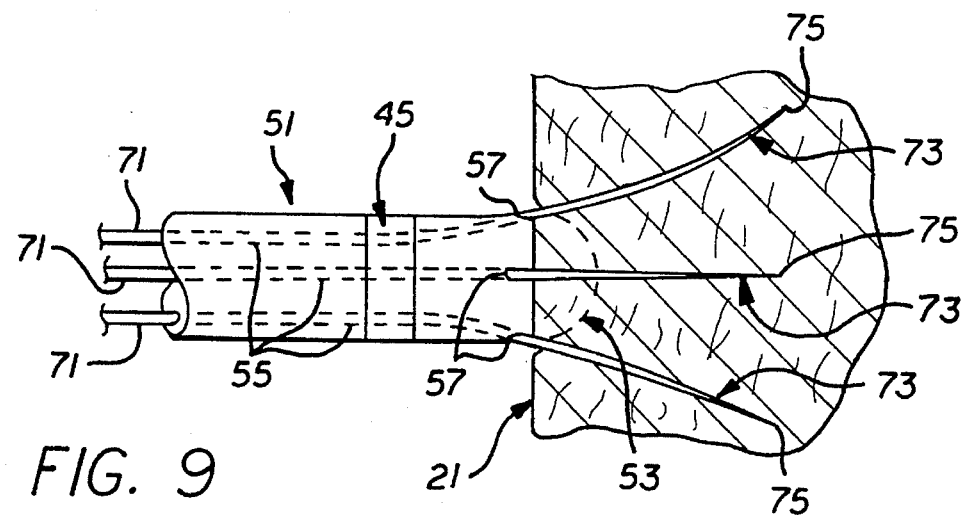

CATHETER TIP STABILIZING APPARATUS

BACKGROUND

This invention generally relates to a catheter apparatus for controllably anchoring and stabilizing a catheter tip relative to a selected tissue.

Medical analysis for the heart muscle has revealed that each normal heart contraction occurs as the result of electrical impulses in the form of a depolarization wave spreading from the atrium to the muscular tissue of the ventricle. In the event that various cells within the heart tissue have been damaged, propagation of the depolarization wave across the heart may be obstructed, leading to irregular heart beat and a condition known as cardiac arrhythmia.

Advances in medical technology for the treatment of cardiac arrhythmia have resulted in the development of various procedures for investigating and remedying the heart's irregular electrical activity. These modern procedures may utilize catheters that are percutaneously introduced into the patient through an artery to the atrium or ventricle of the heart to perform singular or multiple diagnostic, therapeutic, and/or surgical procedures. These catheter devices typically include multiple lumina, or longitudinal passageways, used for different purposes such as carrying electrical wires, body fluids, or drugs.

One medical procedure is known as electrophysiological mapping where a physician analyzes the depolarization waveforms as they propagate across the heart during each contraction. A percutaneously introduced steerable catheter mapping device may be utilized to position an electrode or electrodes for systematically scanning selected endocardial sites within the heart to detect propagation of wave electrical impulses. Through the detection of irregular electrical impulses, the locations of damaged cells may be revealed. Once these damaged cells have been located, the physician may use an ablation procedure to destroy the damaged cells in an attempt to remove the depolarization wave obstruction and bring about a more normal heart beat. The ablation device may be incorporated in the catheter along with the mapping device.

In order for mapping procedures to be effective, the electrode must be precisely located with respect to the tissue and preferably make intimate contact with the endocardial tissue during systematic scanning over various sites. Due to the heart's periodic contraction such precise location is difficult to maintain. This is particularly true when the patient's heart experiences rapid movement during, for instance, tachycardia. Typical procedure requires the physician to manually apply continual axial pressure to the proximal end of the catheter forcing the catheter distal end against the tissue site.

Many catheter ablation devices use radio frequency (RF) technology to destroy damaged endocardial cells. In practice, the catheter distal tip is fitted with an electrode which will emit RF energy to destroy located damaged cells. To be most effective, the electrode at the distal end of an RF ablation catheter is placed in secure intimate contact with the selected endocardial tissue in order to avoid leaving a gap in which concentrated energy might boil the blood in the intracardial volume. Positive maintenance of intimate electrode to tissue contact is further effective to better focus the RF energy to the selected site limiting unnecessary tissue ablation. Positioning of the electrode relative to the tissue can best be achieved by anchoring to the tissue and then shifting the electrode relative to the anchor point. It is desirable to align the catheter tube and attached distal electrode in a perpendicular position relative to the target tissue site so as to accurately discharge RF energy which further limits unnecessary tissue ablation.

Hence, those skilled in the art have recognized the need for anchoring a catheter distal tip to a selected endocardial site. Furthermore, recognized benefits inure in repeatedly positioning and anchoring the catheter distal tip relative to several endocardial sites within a patient's intracardial volume.

SUMMARY OF THE INVENTION

The invention provides anchoring and stabilization of an electrophysiological catheter to the endocardium of the heart and will assist in securing positive contact between the distal tip of the catheter to the endocardium. Moreover, the invention provides a retractable anchor so the distal tip of the catheter can be repetitively located at several selected endocardial tissue sites.

The catheter stabilizing apparatus of the present invention is characterized by a catheter tube having a distal working end for selective location relative to tissue to be treated and a control wire receiving lumen terminating in a distal port. A control wire has a proximal handle located exterior of the patient and extends bodily through the lumen to form at or near, for example, within 3 cm of, its distal extremity a stabilizer foot for selective projection from such distal port. The distal portion of the control wire is formed with a preformed curved resilient foot such that retraction into the lumen will tend to straighten the foot from its curvature but advancement to extend from the distal port will permit such foot to assume its curved configuration for anchoring to such tissue. The catheter, once the foot is anchored, can then be selectively shifted along the control wire, relative to the tissue for careful placement of the working end of the catheter relative to such tissue.

In various embodiments the working end of the catheter mounts electrodes which are operative upon energization thereof to diagnose or treat the tissue. The curved foot may be formed at its distal end with a point such that the foot, when extended from the distal port, will penetrate the tissue in a path defined by the preformed curvature of the foot.

The method of the present invention involves the selection of a catheter of the type having a control wire projecting through a lumen therein and extendable from a distal port to expose a stabilizer foot. The catheter may be introduced utilizing the percutaneous technique to locate the working end of such catheter adjacent tissue to be treated. The control wire is advanced to extend from the distal port to expose the foot to engage the tissue to thereby stabilize the working end of the catheter. The catheter may then be advanced on the control wire to locate the working end thereof in a stabilized position relative to the tissue. This technique may be employed for actually embedding an RF electrode in the tissue or otherwise orienting an electrode in a desired orientation relative to such tissue.

A preformed curved resilient foot may be constructed in a variety of lengths, radii of curvature and resilience to meet the requirements for the particular medical procedure, thus adhering to many different selected tissues. The resilient foot and control wire may be fabricated of pseudo-elastic materials, such as nickel-titanium alloys.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is a diagrammatic view of a human heart partially broken away, including a side view of a catheter tip stabilizing apparatus embodied in the present invention;

FIG. 2 is a broken side view, in enlarged scale, of a control wire included in the catheter tip stabilizing apparatus shown in FIG. 1;

FIGS. 3 and 4 are broken fragmentary side views, in enlarged scale, of a catheter tip stabilizing apparatus shown in FIG. 1 with a control wire shifted to different axial positions;

FIG. 5 is a fragmentary side view of a second embodiment of the catheter tip stabilizing apparatus of the present invention;

FIG. 6 is a transverse sectional view, in enlarged scale, taken along line 6—6 of FIG. 5;

FIG. 7 is a broken side view, partially cut away, of the catheter tip stabilizing apparatus shown in FIG. 5 with the control wires deployed;

FIG. 8 is a side view, in enlarged scale, of a control wire included in the catheter tip stabilizing apparatus shown in FIG. 7; and FIG. 9 is a broken side view, partially cut away, of a third embodiment of the catheter tip stabilizing apparatus of the present invention.

DESCRIPTION OF THE PREFERRED EMBODIMENTS

As shown in the drawings for purposes of illustration, the invention is embodied in an electrophysiology catheter apparatus allowing a user to controllably anchor a catheter distal tip to a selected endocardial tissue. By sliding at least one control wire, including a preformed resilient foot at or near, for example, within 3 cm of, its distal extremity, within a catheter lumen from its retracted position to its advanced position, the preformed resilient foot extends out and beyond a catheter distal port to project laterally and contact the endocardial tissue to provide for stabilization of the distal tip relative to the tissue.

The term "anchor" as used throughout the specification is used in a broad sense and is defined as a device to hold an object securely relative to another body or object. The term "foot" as used throughout the specification is also used in a broad sense and is defined as the physical device that provides "anchoring."

Referring to FIGS. 1–4, the catheter stabilizing apparatus of the present invention is shown, for illustrative purposes, inserted into the left ventricle 21 of a human heart 23 for localized diagnosis or treatment of endocardial tissue at 25. The catheter stabilizer apparatus includes, generally, a catheter tube 27 having a radio frequency (RF) electrode 29 mounted at the working end thereof and formed with a through control wire lumen 31 terminating axially at a distal port 33. Received in the lumen 31 is a control wire, generally designated 35, which is formed on its proximal end with a handle 37 and is formed at or near, for example, within 3 cm of, its distal end with a preformed curved foot, generally designated 39, to be extended to anchor the distal tip of such catheter relative to the tissue.

In treatment of the human heart, it has been common practice to introduce a catheter percutaneously from a cut down site at the patient's groin to be advanced up through the femoral artery, over the aortic arch and down into a heart chamber, for instance the left ventricle, for the purpose of, for instance, electrophysiological mapping of selected areas of the heart tissue. Once this mapping procedure is completed and the data collected analyzed, an ablation procedure may be undertaken to introduce RF current to an electrode at the working end of the catheter to thereby destroy the detected damaged cells to thus remove the depolarization wave obstruction and restore normal heart beat.

Those skilled in the art will recognize that substantial time and effort may be expended in an effort to properly position the working end of the catheter in the precise location within the heart chamber relative to the tissue to be mapped or treated. It is important that the location then be maintained, particularly for the purpose of pinpointing the destructive effect of the electrode as it is applied to the diseased endocardial tissue. The challenge in maintaining the location of the working end of the catheter relative to the endocardial tissue becomes even greater as the heart speeds up as in the case of tachycardia. It is to this end that the stabilizing apparatus of the present invention provides for secure stabilization so that the location within the heart can be maintained while the diagnostic and surgical procedures are undertaken.

The catheter tip stabilizing apparatus of the present invention may incorporate a conventional steerable catheter tube 27 having sufficient torsional rigidity so that rotation of the proximal end will facilitate rotation at the distal end so that it can be directed from the proximal end to manipulate the distal end within a heart chamber such as the ventricle 21. The catheter tube 27 is of sufficient length, as for instance about 60 cm and no less than 30 cm, to allow for a brachial approach to the heart of an adult patient and in the preferred embodiment, is at least 120 cm long to allow for a femoral approach. The catheter tube conventional construction for a steerable catheter to be flexible for translumenal introduction, has to be sufficiently rigid in the distal segment 40 to remain relatively straight so as to overcome the bias in the foot curve to straighten such as it is withdrawn to the retracted position in the catheter tube shown in FIG. 3. Such rigidity may be achieved by incorporating an additional constraining layer of woven mesh to exhibit sufficient rigidity to overcome the bias of the curve.

The catheter tip may include a radiopaque band 45 for imaging under the fluoroscope so the operator can follow the path of the catheter tip within the heart chamber. The lumen 31 may be of a slightly larger diameter than that of the body of the control wire 35 to thus allow for free longitudinal telescopical movement thereof. Although not shown, the catheter tube includes the usual electrical leads leading from the electrode to the proximal end thereof for connection with the mapping electronics or the RF generator, as the case may be.

The handle 37 may be in any desirable form for convenient hand grasping and may, if desirable, be enlarged in diameter and, in some embodiments, will be configured to incorporate a spring loading arrangement such that flipping of a trigger at the proximal end of the catheter will release the control wire 35 for rapid employment in the distal direction under the influence of the spring to thereby facilitate nearly instantaneous anchoring of the catheter tip in the desire location.

The foot 39 formed at or near, for example, with 3 cm of, the distal extremity of the control wire 35 shown in FIG. 4 is preferably configured at its distal end with a point 49 and is formed in a preset curve to turn back on itself to define somewhat of a J-shaped semicircular hook so that it will, upon being projected from the distal port 33 penetrating slightly into the endocardium in a semicircular pattern to securely hook thereinto. This configuration is shown exaggerated for illustrative purposes, it only being important that penetration and hooking be of such a nature as to secure the working end of the catheter to the endocardium with sufficient anchoring force to cause the catheter tip to follow the undulating endocardium during the rhythmic heart beat. The radius of curvature may be of various degrees of tightness, for instance, covering a range of 0.5 cm to 1 cm. In the preferred embodiment the curve, in its unstressed condition, has a radius of curvature of 0.5 cm and forms about one half of a circle to thus define an effective hook.

The hook shaped foot 39 is preferably constructed of pseudo-elastic material such as a nickel titanium alloy such as that sold under the trade designation (NITINOL) and available from Shape Memory Alloys, Inc. whose address is 1034 W. Maude Avenue, Suite 603, Sunnyvale, Calif. 94086. This alloy of about nickel is known in the art as being of such a nature as to allow for repeated deformation and yet return to its original shape each time the load thereon is released. Alloys of this type vary, having 30–52% titanium, 38–52% nickel, 0–20% copper, and 0–10% of other alloy elements such as a group consisting of 0—3% each of iron, cobalt, chromium, palladium, zirconium, hafnium, and niobium.

In operation, the control wire 35 is retracted proximally in catheter tube 27 and the catheter introduced percutaneously, as by the Seldinger cut down in the groin area to be passed translumenally up the aorta, over the aortic arch and down into the ventricle 21. The catheter is manipulated from the proximal end exterior of the patient's body to manipulate the distal tip under fluoroscopic observation to position the distal tip in axial alignment with the specific tissue 25 to be mapped (FIG. 3). The catheter may well be pressed firmly against the surface of the endocardium by pushing on the proximal end thereof (FIG. 4). The control wire handle 37 may then be grasped and the control wire advanced telescopically relative to the catheter tube to thus project the sharp point 49 of the foot 39 from the distal port 33 to thus penetrate the tissue 25 forming the wall of the ventricle. As telescopical extension of the control wire 35 is continued, the inherent stress in the foot 39 will cause it to curve resulting in a penetration path within the tissue which is likewise curved thus leading to a generally J-shaped hook for the fully extended foot as shown in FIG. 4.

It will be appreciated that the catheter tube 27 may then be advanced or retracted on the control wire as desired to obtain the desired positioning for the electrode for the procedure to be performed. As an example, for mapping, the electrode 29 is positioned at the endocardium surface to sense the wave form transmitted through the adjacent tissue so that data can be gathered and analyzed. Once located at the desired position on the control wire 35, the catheter may be locked in position as by a clamp or the like to maintain it telescoped in position on the control wire. Then, the tip of the catheter will be maintained in alignment on the control wire as shown in FIG. 4 to be maintained in position generally perpendicular relative to the surface of the endocardium. It will be appreciated that with the foot 39 hooked into the endocardium and the catheter tube 27 telescoped to its extended position the electrode 29 imbedded in the soft tissue. It is an advantage that any desired spacing from the surface of the tissue may thus be maintained irrespective of fluctuations in the relative location of that tissue since hooking by the foot 39 of the distal tip will cause such distal tip to follow the heart wall even during erratic fluctuation thereof such as in the event of tachycardia. It will be appreciated that with the electrode 29 securely locked in position relative to the endocardium, the electrophysiological mapping may be undertaken with the data generated retrieved through the electrical leads (not shown) to be displayed, recorded, and analyzed by the physician.

For the catheter shown, the electrode 29 also serves as an RF ablation electrode. Consequently, after the data has been analyzed, the controls on the power source may be switched to apply the desired RF to the electrode 29 to thus provide for precise and controlled treatment. That is, the catheter tube 27 may be advanced on the anchored control wire 35 a distance sufficient to fully embed the tip of the electrode 29 within the tissue 25 such as to maintain it in positive intimate contact without spacing therebetween within which blood might circulate and be subjected to high energy and consequent severe damage due to elevated temperatures. Again, the electrode will be held positively in position irrespective of erratic movement of the heart wall.

The distal extremity of the catheter tube 27 has a certain degree of semi-rigidity to the point where it will overcome the inherent bias of the pseudo-elastic foot section 39 upon retraction thereof into the distal segment 40 to thus effect straightening to form a linear configuration as it is withdrawn into the lumen 31. This produces a straightening effect on the foot 39 as it is withdrawn from the position shown in FIG. 4 such that the foot will tend to be flexed from the curved path punctured in the endocardium to assume a progressively straighter configuration as withdrawal is continued to thereby provide for retraction out the path cut in the tissue to avoid the trauma which would be otherwise associated with withdrawal of the hook shaped foot. The straightening of such foot and retraction thereof will thus release the distal tip of the catheter from the endocardium thereby freeing the catheter itself for withdrawal from the ventricle and out the aortic arch, through the aorta and femoral artery.

Referring to FIG. 5, a second embodiment of the catheter stabilizing apparatus of the present invention includes, generally, a catheter tube 51 mounting at the distal tip an electrode 53 and formed with four longitudinally extending lumens 55 formed in their respective distal extremities with radially outwardly curved lumen segments 57 which terminate in respective radially outwardly opening distal ports 59 disposed equidistant about such tube. Control wires, generally designated 61 are received telescopically in the respective lumens 55 and mount on their proximal ends respective handles 63. The control wires 61 are shown ganged together at their respective proximal ends by means of a connector web 65 such that the wires may be moved longitudinally in unison. In an alternative embodiment the respective control wires 61 are unconnected and move freely relative to one another.

As with the embodiment shown in FIGS. 1–4, the control wires 65 are constructed of pseudo-elastic material such as a nickel titanium alloy and are formed at or near, for example, within 3 cm of, their respective distal extremities with preformed curved feet, generally designated 67, so as to, in their extended position, curve radially outwardly from the axial direction of the catheter. The respective flattened stabilizing feet 67 are formed at their distal ends with respective flattened stabilizing pads 69 which are configured to engage and press against the surface of the endocardium to thereby maintain the distal end of the catheter oriented perpendicular to the surface of the endocardium.

The respective feet 69 are rounded and slightly enlarged so as to, for this application, avoid penetration of the endocardium but yet provide for solid surface contact therewith. The respective curved feet 67 are of a uniform cross-sectional configuration and curvature so that each foot, when projected to the advanced position shown in FIG. 7, affords a similar bias and consequent force on the catheter tube so that the lateral component of force from each of the four sides of the catheter is substantially equal whereby the catheter will be maintained generally perpendicular to the surface of the endocardium.

In operation, the catheter of FIGS. 5–8 will be inserted with the control wires 61 in their fully retracted positions as shown in FIG. 5 and with the respective feet 67 retracted within the respective control wire lumens as viewed in FIG. 5. Typically, the catheter will be of the steerable type and will be inserted by a translumenal percutaneous procedure and advanced into the left ventricle to be maneuvered under fluoroscopic observation to position the tip generally confronting the tissue to be treated. By pressing axially on the proximal end of the catheter projecting from the patient's body, the distal tip may be driven in to the soft tissue as shown in FIG. 7. Orientation of such distal tip may be maintained by advancing the control wires 61 as a unit thus causing the respective feet 67 to be projected radially outwardly in the lumen segments 58 to exit the radially opening distal ports 57 to thus assume their generally curved configuration curving radially outwardly and distally as shown in FIG. 7 to contact the surface of the endocardium. By holding the control wires in their respective advanced positions as shown in FIG. 7, as by clamping them in position relative to the catheter tube, constant force will be maintained on the distal tube segment to maintain it generally erect or perpendicular to the surface of the endocardium. This serves to maintain a strut-like radial bracing configuration on the catheter in such a manner that the catheter itself may be advanced or retracted as desired on the control wires while still maintaining a desired orientation which, in this instance, happens to be perpendicular to the endocardium surface. This feature thus provides for positive orientation of the catheter tip and, consequently, the electrode 53 irrespective of rapid or erratic undulation of the endocardium, as might result from tachycardia, so that treatment of the endocardium may be reliably continued in a accurately focused area of tissue without dislodgement and reorientation each time the endocardium is subjected to rigorous movement.

The catheter tip stabilizing apparatus shown in FIG. 9 is similar to that shown in FIG. 5 except that the control wires, generally designated 71, are formed at or near, for example, within 3 cm of, their distal extremities with their respective pre-curved feet, generally designated 73, formed at their respective tips with points 75 for penetrating the endocardium. The pre-shaped curves in the respective feet 73 are of a relatively large radius of curvature, for instance, having a value of, for instance 30 cm to cause them to angle only slightly from a straight line to about 1 cm. For the larger radius of curvatures the semi-rigid character of the catheter will serve to maintain the feet relatively straight for some distance from the distal ports 57 to a point where a sufficient length of hook has been extended to allow the pre-stress in the hook to cause the very distal portion of the foot to assume a slight curvature as shown in FIG. 8 but without reversing on itself in hook position. Advancement of the respective such feet will thus cause the respective points to cut respective paths which are first relatively straight and which then curve outwardly away from one another to curve paths with a minimum of trauma to the surrounding tissue. The combined radially outwardly directed array of deployed hooks will serve as a positive anchor against unwanted disengagement of the catheter from the endocardium. This relatively large radius of curvature for the respective feet 73 and consequent configuration upon deployment as shown in FIG. 9 will serve to minimize tissue injury, both during deployment and during retraction, while affording a relatively positive releasable anchoring system. As above, the electrode 53 can be reliably and accurately positioned relative to the tissue and will be securely maintained in place relative to the tissue surface. While so positioned, the waveforms from the tissue can be mapped to provide a reliable indication of the quality of the tissue targeted. Thereafter, the catheter may be employed to ablate the diseased tissue detected. To this end the catheter tube 51 can be advanced and clamped into the position on the control wires 71 at the position shown at FIG. 9 so as to positively embed the electrode 53 depressed beneath the normal surface of the endocardium to thereby provide a layer of tissue about the entire exposed surface of such electrode and avoid contact of any substantial amounts of blood with such electrode. As noted above, this feature tends to minimize heating of the blood and consequent damage due to elevated temperatures.

When the catheter 51 is to be removed, the operator may merely grasp the proximal handles and withdraw the control wire 71 proximally to thus draw the respective feet 73 proximally from the respective paths defined by such feet as the point 75 penetrated the endocardium. The relatively large radius of curvature will, as the feet are withdrawn, cause the distal extremities to be straightened somewhat to cause such feet to closely follow the respective paths cut by the points 75 on entry to thereby minimize the tendency of the sharp point 75 to cut into the endocardium during retraction. Upon full retraction of the control wire 71 the respective feet 73 will be fully retracted within the respective distal ports 57 and will be constrained in the relatively straightened configuration defined by the respective control wire lumens 55.

From the foregoing it will be apparent that the stabilizing catheter apparatus of the present invention provides a convenient and reliable arrangement for locating the working tip of a catheter relative to the endocardium and provides for reliable and positive orientation thereof irrespective or erratic and rapid movement of the endocardium wall.

Although the apparatus was described and shown as operating with a catheter having an RF ablation electrode 29, the stabilizing catheter apparatus is also usable with other types of catheters. For example, the apparatus may be incorporated in a catheter using ultrasound transducers or optical devices. Additionally, the stabilizing catheter apparatus may be used in imaging catheters or other types of catheters used in electrophysiology studies. Catheters performing only mapping or only ablation functions may incorporate the apparatus in accordance with the invention.

The invention may be embodied in other specific forms without departing from the spirit or essential characteristics thereof. For example, a preformed curved resilient foot may be constructed of many different pseudo-elastic materials, and a control wire handle may be spring loaded in such a manner to release a resilient foot to its advanced position under spring tension. The present embodiments are therefore considered in all respects as illustrative and not restrictive, the scope of the invention being indicated by the foregoing description, and all changes which come within the meaning and range of equivalency of the claims are therefore intended to be embraced therein.

What is claimed is:

1. A catheter tip stabilizing apparatus for releasably anchoring such tip to tissue, comprising:

a catheter having proximal and distal ends and formed with a lumen extending therethrough;

an electrode tip affixed to the distal end of said catheter, and having a port formed therein in communication with said lumen;

a straightening segment affixed to the distal end of said catheter;

a control wire having proximal and distal ends slidably received within said lumen and having a foot formed at its distal end, wherein said foot is formed with a point for, when said wire is in an advanced position, penetrating said tissue to cut a path for said foot to extend thereinto, and wherein said foot is in the form of a preformed curve having, in its unstressed configuration, a radius of curvature sufficiently small to form a turned back tip portion to act as a hook whereby retraction of said control wire to a retracted position will draw said foot into said straightening segment to flex said foot from said preformed curve to a straightened configuration, and advancement of said wire to an advanced position will extend said foot from said port to free said wire to assume said preformed curve to, when penetrating said tissue, act as said hook, thereby engaging the tissue in a stabilizing manner whereby, upon positioning said electrode tip against tissue and longitudinally advancing said control wire in a distal direction, said foot is caused to extend outwardly through said port in said electrode tip to engage said tissue to prevent said electrode tip from becoming dislodged.

2. The apparatus of claim 1 wherein;

said control wire is constructed of pseudo-elastic material.

3. The apparatus of claim 2 wherein;

said control wire is constructed of a nickel-titanium alloy.

4. The apparatus of claim 1 wherein;

said foot is in the form of a preformed curve having a radius of curvature at least between 0.05 cm and 1 cm.

5. The apparatus of claim 1 wherein;

said preformed curve is formed within 3 cm of said distal end of said wire.

6. The apparatus of claim 1 that wherein said electrode comprises an ablating electrode.

7. A catheter tip stabilizing apparatus for releasably anchoring such tip to tissue, comprising;

a catheter having proximal and distal ends formed with a lumen extending therethrough in communication with ports formed in its exterior near its distal end;

an electrode tip affixed to the distal end of said catheter; and control wires having proximal and distal ends, slidably received within said lumen configured to each access one of said ports and each having a foot formed near its distal end, such foot configured to engage the tissue in a stabilizing manner wherein said control wires are connected together near their respective proximal ends and wherein said feet are resilient and are configured in preformed curves said wires arranged and configured so that their proximal ends may be grasped to draw said wires in a proximal direction to respective retracted positions in said catheter to flex said feet from the respective said preformed curves to be received within said catheter and to, alternatively, advance said wires distally to respective advanced positions to shift said feet out the respective said ports free of said catheter to assume the respective said preformed curves to project laterally contacting said tissue to locate said electrode tip relative to said tissue and wherein said feet are formed at their respective distal ends with points for, when said control wires are in the advanced positions, penetrating said tissue, whereby, upon positioning said electrode tip against tissue and longitudinally advancing said control wires in a distal direction, said feet are caused to extend radially outwardly from said catheter to engage said tissue and prevent said electrode tip from becoming dislodged from a substantially perpendicular position relative the tissue.

8. A catheter tip stabilizing apparatus for releasably anchoring such tip to tissue, comprising:

a catheter having proximal and distal ends formed with a lumen extending therethrough in communication with ports formed in its exterior near its distal end;

an electrode tip affixed to the distal end of said catheter; and control wires having proximal and distal ends, slidably received within said lumen configured to each access one of said ports and each having a foot formed near its distal end, such foot configured to engage the tissue in a stabilizing manner wherein said control wires are connected together near their respective proximal ends and wherein said feet are resilient and are configured in preformed curves, said wires arranged and configured so that their proximal ends may be grasped to draw said wires in a proximal direction to respective retracted positions in said catheter to flex said feet from the respective said preformed curves to be received within said catheter and to, alternatively, advance said wires distally to respective advanced positions to shift said feet out the respective said ports free of said catheter to assume the respective said preformed curves to protect laterally contacting said tissue to locate said electrode tip relative to said tissue, and wherein said feet are constructed of pseudo-elastic nickel-titanium alloy, whereby, upon positioning said electrode tip against tissue and longitudinally advancing said control wires in a distal direction, said feet are caused to extend radially outwardly from said catheter to engage said tissue and prevent said electrode tip from becoming dislodged from a substantially perpendicular position relative the tissue.

9. A method of stabilizing a catheter tip relative to a selected tissue including;

selecting a catheter apparatus of the type, including a catheter tube distally terminating a catheter tip, and at least one elongated control wire having proximal and distal ends and received telescopically therein, having a handle at the proximal end and an elongated, resilient foot, adjacent the distal end, said foot preformed with a curve terminating in a point wherein upon telescoping of said wire to an advanced position, said foot is shifted to a stabilizing position extended from said catheter tube to assume said the preformed curve;

with said wire retracted to retract foot into said catheter tube, maneuvering said catheter apparatus into the body of a patient so as to position said catheter tip adjacent said tissue in position substantially perpendicular to such tissue; and advancing said wire a sufficient distance relative to said catheter tube to cause said point to penetrate said tissue to cut a path therein for said foot and then advancing said control wire to cause said foot to become anchored in said tissue to locate said catheter tip relative to said tissue.

10. A method of stabilizing a catheter tip relative to a selected tissue including:

selecting a catheter apparatus of the type including a catheter tube distally terminating in a catheter tip, and at least one elongated control wire having proximal and distal ends and received telescopically therein having a handle at the proximal end and an elongated, resilient preformed curved foot terminating in a point for penetrating said tissue to anchor said catheter thereto said foot being adjacent to the distal end for being, upon telescoping of said wire to an advanced position, shifted to a stabilizing position extended from said catheter tube to assume said the preformed curve;

with said wire retracted to retract said foot into said catheter tube, maneuvering said catheter apparatus into the body of a patient so as to position said catheter tip adjacent said tissue in position substantially perpendicular to such tissue; and advancing said wire to said advanced position extending said foot distally from said catheter tube a distance sufficient to extend said foot to said stabilizing position, to thereby penetrate said point into said tissue to cut a path for said foot to engage said tissue and stabilize the position of said catheter tip relative thereto.

* * * * *